United States Patent
Jung et al.

(10) Patent No.: US 9,493,767 B2
(45) Date of Patent: Nov. 15, 2016

(54) METHOD FOR SCREENING FOR HIGH L-TRYPTOPHAN PRODUCING MICROORGANISMS USING RIBOSWITCH

(71) Applicant: POSTECH ACADEMY-INDUSTRY FOUNDATION, Gyeongsangbuk-do (KR)

(72) Inventors: Gyoo Yeol Jung, Seoul (KR); Jina Yang, Jeju-do (KR); SungHo Jang, Gyeongsangbuk-do (KR); Sang Woo Seo, Seoul (KR)

(73) Assignee: POSTECH ACADEMY-INDUSTRY FOUNDATION, Gyeongsang buk-do (KR)

( * ) Notice: Subject to any disclaimer, the term of this patent is extended or adjusted under 35 U.S.C. 154(b) by 28 days.

(21) Appl. No.: 14/406,422

(22) PCT Filed: Jun. 19, 2013

(86) PCT No.: PCT/KR2013/005423
§ 371 (c)(1),
(2) Date: Dec. 8, 2014

(87) PCT Pub. No.: WO2013/191473
PCT Pub. Date: Dec. 27, 2013

(65) Prior Publication Data
US 2015/0337293 A1    Nov. 26, 2015

(30) Foreign Application Priority Data

Jun. 20, 2012 (KR) .................. 10-2012-0066009
Jun. 18, 2013 (KR) .................. 10-2013-0069803

(51) Int. Cl.
*C12N 15/11* (2006.01)
*C12N 15/10* (2006.01)
*C12N 15/115* (2010.01)

(52) U.S. Cl.
CPC ......... *C12N 15/1048* (2013.01); *C12N 15/115* (2013.01); *C12N 2310/16* (2013.01); *C12N 2310/3519* (2013.01); *C12N 2320/10* (2013.01); *C12N 2320/13* (2013.01); *C12N 2330/31* (2013.01)

(58) Field of Classification Search
None
See application file for complete search history.

(56) References Cited

FOREIGN PATENT DOCUMENTS

KR    10-2010-0017905 A    2/2010

OTHER PUBLICATIONS

Jang et al., "Engineering of L-Tryptophan Aptamer to Produce RNA Switch", Korea Society for Biotechnology and Bioengineering Spring Meeting, Abstracts, p. 189, (2011).
Majerfeld et al., "A diminutive and specific RNA binding site for L-tryptophan", Nucleic Acids Research, vol. 33, No. 17, pp. 5482-5493, (2005).
Muranaka et al., "An efficient platform for genetic selection and screening of gene switches in *Escherichia coli*", Nucleic Acids Research, vol. 37, No. 5, e39, (2009).
Korean Official Action for Korean Application No. 10-2013-0069803, four pages, mailed Aug. 29, 2014.
Weigand et al., "Screening for engineered neomycin riboswitches that control translation initiation", RNA, vol. 14, pp. 89-97, (2008).

*Primary Examiner* — Nancy Treptow
(74) *Attorney, Agent, or Firm* — Vorys, Sater, Seymour & Pease LLP; Mih Suhn Koh

(57) ABSTRACT

A method of screening a high L-tryptophan-producing microorganism using a riboswitch is provided. More particularly, a riboswitch for screening a high L-tryptophan-producing microorganism including a tryptophan aptamer, a DNA sequence consisting of 1 to 20 nucleotides and a selectable marker gene, and a method of screening a high L-tryptophan-producing microorganism using the same are provided. The riboswitch and the method of screening a high L-tryptophan-producing microorganism using the same can be useful in selecting a strain producing a high concentration of L-tryptophan in a relatively quick and easy manner, and thus enhancing price competitiveness of tryptophan production using microorganisms.

4 Claims, 10 Drawing Sheets

Fig. 3
① 5' KpnI - SD - tetA - linker(GGGS)*4 3'    ② 5' linker(GGGS)*4 - sGFP - SacI 3'
③ Overlap PCR
5' KpnI - SD - tetA - linker(GGGS)*4 - sGFP - SacI 3'
④ TA Cloning
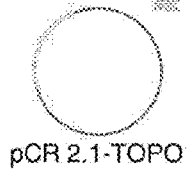    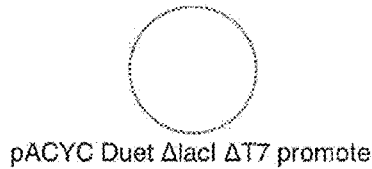
pCR 2.1-TOPO       pACYC Duet ΔlacI ΔT7 promoter
⑤ Digestion by KpnI and SacI          ⑥ Digestion by KpnI and SacI
    
⑦ Ligation by T4 ligase
⑧ PCR
Promoter-Aptamer-N10-SD-tetA-sGFP-pACYC
⑨ Blunt-end Ligation
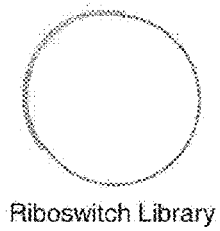
Riboswitch Library
⑩ Transformation into MegaX DHα 10B Colony PCR result for pMD20-tetA-linker-sGFP TA clones
tetA(1191bp) + sGFP(720bp) + linker(48bp) = 1959 pMD20-tetA-sGFP Enzyme Cut pACYC-tetA-sGFP Colony PCR

PCR product ≈ 4.4kb

METHOD FOR SCREENING FOR HIGH L-TRYPTOPHAN PRODUCING MICROORGANISMS USING RIBOSWITCH

The Sequence Listing submitted in text format (.txt) filed on Mar. 19, 2015, named "SequenceListing$_{13}$ Eruum.txt", created on Mar. 19, 2015, 6.42 KB), is incorporated herein by reference.

TECHNICAL FIELD

The present disclosure relates to a method of screening a high L-tryptophan-producing microorganism using a riboswitch, and more particularly, to a riboswitch for screening a high L-tryptophan-producing microorganism including a tryptophan aptamer, a DNA sequence consisting of 1 to 20 nucleotides and a selectable marker gene and a method of screening a high L-tryptophan-producing microorganism using the same.

BACKGROUND ART

Development of strains has been continuously conducted to enhance price competitiveness of methods of producing metabolites using microorganisms. A conventional and effective combinational approach for developing new strains includes producing a strain library based on a producing strain and screening strains having improved characteristics from the strain library. For example, the combinational approach includes a case of development of a monosodium glutamate (MSG)-producing strain using a production method converted from an extraction method of the 1960s to a fermentation method using microorganisms.

To produce the strain library, UV irradiation, methods such as chemical mutagenesis including adding a chemical mutagen such as nitrosoguanidine (NTG), and the like were used in the past. In modern times in which biomolecular tools and biochemical knowledge have been accumulated, various methods of producing a strain library, such as mutagenesis of genes based on a polymerase chain reaction (PCR), genome shuffling using protoplast fusion, and random insertion using a transposon have been proposed. A strain library may be produced using the diverse methods of producing a strain library described above since the probability of the strain library including the high target-metabolite-producing microorganisms increases with an increase in size of the strain library.

Various analysis methods have been used to determine the productivity of a target metabolite in a strain. Liquid/gas chromatography (LC/GC) is a method of culturing individual strains and analyzing concentrations of metabolites in a culture broth and the strain. Such a method is available for quantitative analysis when it can be used to detect most of the metabolites and obtain a standard assay curve. However, the method can be used to analyze only one mutant strain at a time, and thus is inefficient for analysis of a library of strains greater than a predetermined size due to low throughput.

A method of analyzing a metabolite using multiplates is a method of analyzing a change in concentration of the metabolite in a sample, which includes putting a mutant strain into partitioned wells and measuring a change in chromogenesis, optical density or fluorescence intensity of a small amount of the sample. Since a small amount of the sample and the multiplates are used, relatively many mutant strains can be analyzed at the same time. However, the method has a problem in that its throughput capacity is insufficient to analyze a library of strains having a large size prepared by the production method. Also, the production method has a narrow application since a chromogenic reaction can be performed using the metabolite as a substrate, or it is applicable to metabolites in which a change in optical density or fluorescence intensity can be measured.

A method of screening a producing strain using a genetic biosensor is used to immediately convert a concentration of a synthesized target metabolite into a detectable signal and detect the detectable signal. When a biosensor specific to a target metabolite is developed and used, a proper detector may be employed to observe a change in concentration of the target metabolite which cannot be detected visually.

A fluorescence-activated cell sorting (FACS) technique is used to detect the fluorescence emitted from individual strains while allowing mutant strains to flow through a detector. Such a technique has a throughput capacity of more than $10^9$ cells since the fluorescence may be detected quickly while allowing a large amount of cells to flow at the same time. When the target metabolite emits the fluorescence, a large library can be analyzed in a relatively quick and easy manner. Thus, it is possible to efficiently screen the high target metabolite-producing microorganism. However, such a technique has a problem in that it is applicable only to metabolites emitting fluorescence.

Finally, a selection method may be used. Such a method is technology designed such that only the strains producing a high concentration of a target metabolite in the strain library survive. Such a method has a very high throughput, and thus may be used to effectively screen only the high target metabolite-producing microorganisms from a library of strains having large sizes. However, such technology can be applied only when the concentration of the target metabolite is associated with the growth or survival of the strains.

Meanwhile, a riboswitch is a biosensor for sensing a concentration of a certain metabolite in cells and regulating expression levels of genes positioned downstream from the riboswitch, and has very high specificity and affinity to substrates. Also, techniques of producing aptamers binding to a certain metabolite using a systematic evolution of ligand by exponential enrichment (SELEX) technique, and constructing riboswitches based on the aptamers have been developed. Therefore, it is possible to develop a riboswitch capable of specifically and sensitively sensing only a metabolite which the present applicant wish to screen and regulating expression levels of genes positioned downstream from the riboswitch.

When a selectable marker gene is inserted downstream from the riboswitch developed thus, it is possible to obtain an RNA device capable of regulating the expression of the selectable marker gene according to the concentration of a target metabolite. When the RNA device is introduced into the strain libraries produced using the various methods, the expression level of the selectable marker gene varies according to the concentration of the target metabolite in each strain. In this case, when a strain candidate transformed with an artificial selection circuit is exposed to a suitable selective pressure to adapt to the selectable marker gene of the RNA device, only the strains producing a high concentration of the target metabolite will survive.

DISCLOSURE

Technical Problem

To solve the problems of the prior art, the present applicant seek to develop a screening technique, which is applicable to various target metabolites and has a high throughput.

Therefore, the present disclosure is directed to a riboswitch for screening a high L-tryptophan-producing microorganism.

Also, the present disclosure is directed to a method of effectively screening a high L-tryptophan-producing microorganism using the riboswitch.

However, the technical objects of the present disclosure are not limited thereto, and other objects of the present disclosure which are not disclosed herein will become more apparent to those of ordinary skill in the art by describing in detail exemplary embodiments thereof.

Technical Solution

According to an aspect of the present disclosure, there is provided a riboswitch for screening a high L-tryptophan-producing microorganism, which includes a tryptophan aptamer, a DNA sequence consisting of 1 to 20 nucleotides, and a selectable marker gene.

According to one exemplary embodiment of the present disclosure, the tryptophan aptamer may be set forth in SEQ ID NO: 2, SEQ ID NO: 13, or SEQ ID NO: 15.

According to another exemplary embodiment of the present disclosure, the DNA sequence consisting of 1 to 20 nucleotides is preferably a DNA sequence consisting of 10 nucleotides, and may be set forth in SEQ ID NO: 3, SEQ ID NO: 4, or SEQ ID NO: 5, but the present disclosure is not limited thereto.

According to still another exemplary embodiment of the present disclosure, the selectable marker gene may include a tetA gene, but the present disclosure is not limited thereto.

According to another aspect of the present disclosure, there is provided a method of screening a high L-tryptophan-producing microorganism using the riboswitch including a tryptophan aptamer, a DNA sequence consisting of 1 to 20 nucleotides, and a selectable marker gene.

According to one exemplary embodiment of the present disclosure, the tryptophan aptamer may be set forth in SEQ ID NO: 2, SEQ ID NO: 13, or SEQ ID NO: 15.

According to another exemplary embodiment of the present disclosure, the DNA sequence consisting of 1 to 20 nucleotides is preferably a DNA sequence consisting of 10 nucleotides, and may be set forth in SEQ ID NO: 3, SEQ ID NO: 4, or SEQ ID NO: 5, but the present disclosure is not limited thereto.

According to still another exemplary embodiment of the present disclosure, the selectable marker gene may include a tetA gene, but the present disclosure is not limited thereto.

Advantageous Effects

The riboswitch and the method of screening a high L-tryptophan-producing microorganism using the same can be useful in selecting a strain producing a high concentration of L-tryptophan in a relatively quick and easy manner, and thus enhancing price competitiveness of tryptophan production using microorganisms.

DESCRIPTION OF DRAWINGS

FIG. 3 is a schematic view showing a cloning procedure for constructing the riboswitch library according to one exemplary embodiment of the present disclosure;

BEST MODES OF THE PRESENT DISCLOSURE

Figure 1:
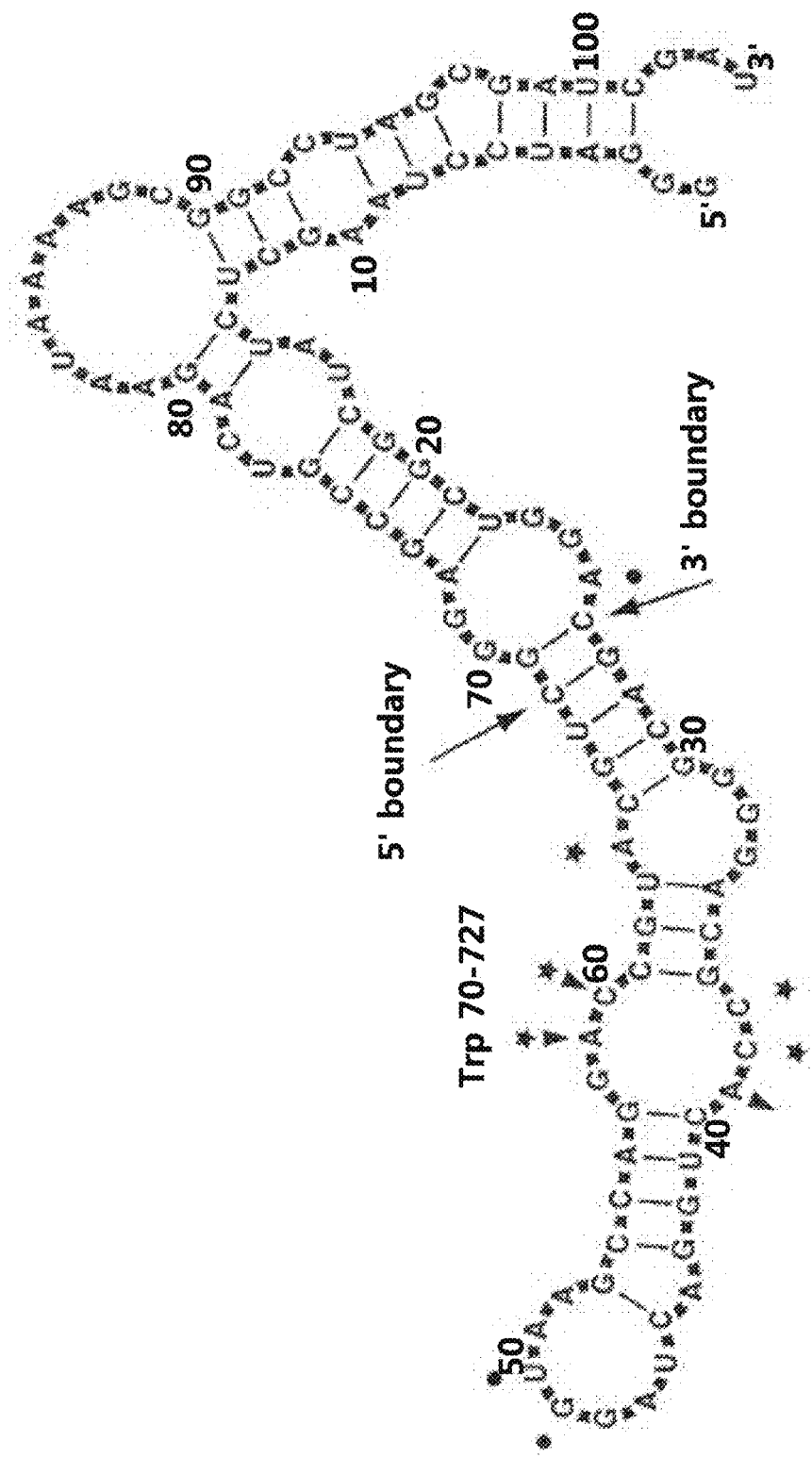
FIG. 1 is a diagram showing a structure of an L-tryptophan aptamer (Trp 70-727). An RNA sequence of the L-tryptophan aptamer (Trp 70-727) is set forth in SEQ ID NO: 1.

The present applicant have developed an RNA switch regulating expression levels of genes positioned downstream from the RNA switch by specifically recognizing L-tryptophan. First, a library having a probability of becoming a switch is constructed using an L-tryptophan RNA aptamer known in the prior art. Then, only switches that actually operate are selected from the library.

The present disclosure provides a riboswitch for screening a high L-tryptophan-producing microorganism, which includes a tryptophan aptamer, a DNA sequence consisting of 1 to 20 nucleotides, and a selectable marker gene.

According to one exemplary embodiment of the present disclosure, the tryptophan aptamer is preferably set forth in SEQ ID NO: 2, SEQ ID NO: 13, or SEQ ID NO: 15.

According to another exemplary embodiment of the present disclosure, the DNA sequence consisting of 1 to 20 nucleotides is preferably a DNA sequence consisting of 10 nucleotides, and may include a DNA sequence set forth in SEQ ID NO: 3, SEQ ID NO: 4, or SEQ ID NO: 5, but the present disclosure is not limited thereto.

According to still another exemplary embodiment of the present disclosure, the selectable marker gene may include a tetA gene encoding a tetracycline resistance protein, but the present disclosure is not limited thereto.

Also, the present disclosure provides a method of screening a high L-tryptophan-producing microorganism using the riboswitch which includes a tryptophan aptamer, a DNA sequence consisting of 1 to 20 nucleotides, and a selectable marker gene.

According to one exemplary embodiment of the present disclosure, the tryptophan aptamer is preferably set forth in SEQ ID NO: 2, SEQ ID NO: 13, or SEQ ID NO: 15.

According to another exemplary embodiment of the present disclosure, the DNA sequence consisting of 1 to 20 nucleotides is preferably a DNA sequence consisting of 10 nucleotides, and may include a DNA sequence set forth in SEQ ID NO: 3, SEQ ID NO: 4, or SEQ ID NO: 5, but the present disclosure is not limited thereto.

According to still another exemplary embodiment of the present disclosure, the selectable marker gene may include a tetA gene encoding a tetracycline resistance protein, but the present disclosure is not limited thereto.

Hereinafter, preferred Examples are provided to aid in understanding the present disclosure. However, it should be understood that detailed description provided herein is merely intended to provide a better understanding of the present disclosure, and not to limit the scope of the present disclosure.

A Taq polymerase, a Phusion polymerase, and restriction enzymes used in the present disclosure were purchased from TaKaRa Bio Inc. or New England Biolabs, pACYC_Duet and pCDF_Duet vectors were purchased from Novagen, and oligonucleotides were synthesized by Genotech Co. Ltd. In addition, components used to prepare a culture broth were all purchased from Sigma-Aldrich.

EXAMPLE 1

Construction of RNA Device Library

First of all, a library having various sequences was constructed to prepare a switch regulating expression levels of genes positioned downstream from the switch according to the concentration of L-tryptophan. The library was constructed by inserting a random sequence having a length of 10 bp (base pairs) between an already known L-tryptophan aptamer (Irene Majerfeld and Michael Yarus, Nucl. Acids. Res., 2005) and a downstream selectable marker gene (tetA-sGFP fusion: SEQ ID NO: 6).

The L-tryptophan aptamer (Trp 70-727) is set forth in SEQ ID NO: 1 and shown in FIG. 1, and provides a site to which L-tryptophan can bind. In a cloning operation according to one exemplary embodiment of the present disclosure, a sequence (SEQ ID NO: 2) in which U residues in the RNA sequence of the L-tryptophan aptamer were substituted with T residues was used. In the downstream selectable marker gene, the tetA gene was used to select sequences acting as riboswitches (RNA switches), and sGFP ligated to the tetA gene was used to examine the performance of the riboswitches selected using fluorescence. The random sequence with the length of 10 bp was positioned upstream from a ribosome binding site (RBS).

Figure 2:
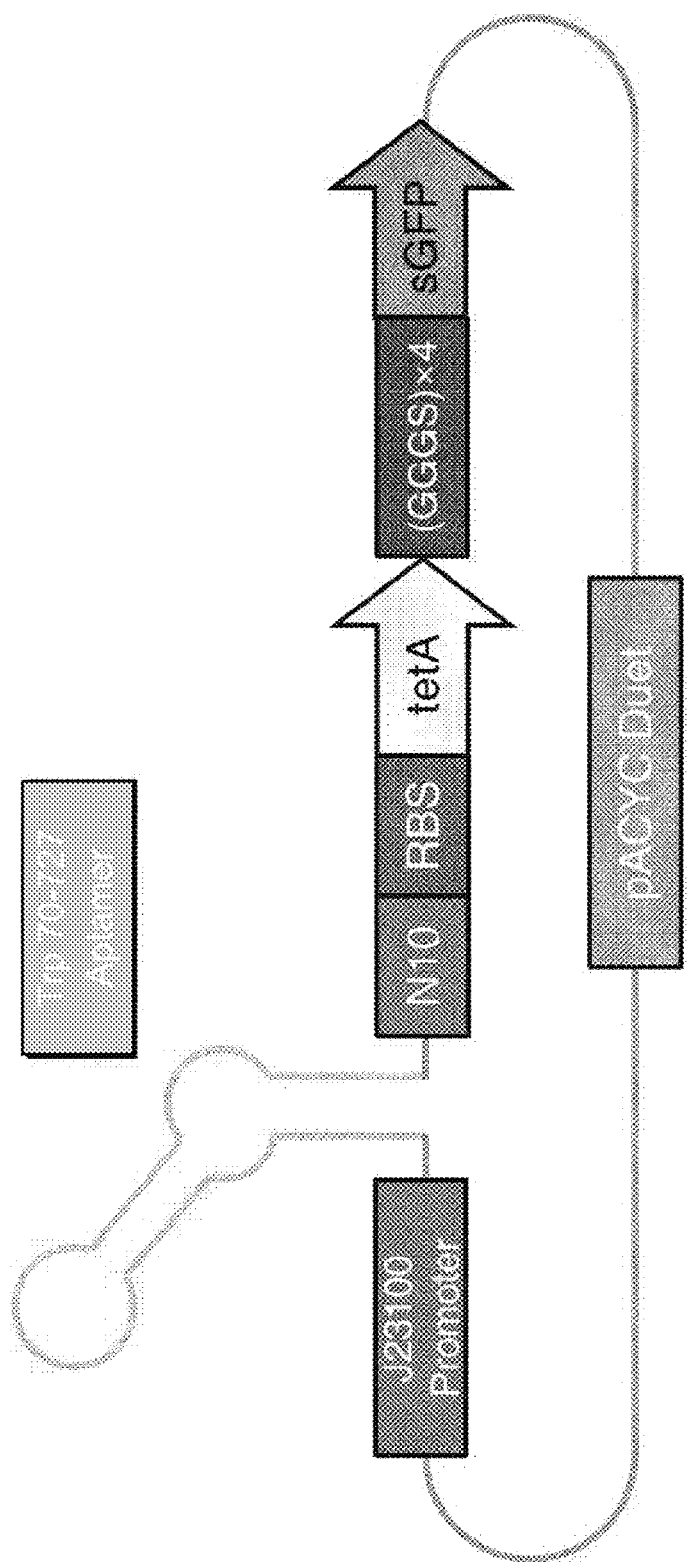
FIG. 2 shows a restriction map of a riboswitch library according to one exemplary embodiment of the present disclosure.

When L-tryptophan is bound to an aptamer, some of random sequences function to trap RBS in a secondary or tertiary structure by complementary binding to the RBS, or expose the RBS to the outside. When the RBS is trapped in the secondary or tertiary structure or exposed to the outside, an influence is exerted on the binding of ribosome, thereby regulating an expression level of a downstream selectable marker gene (a tetA-sGFP fusion). A restriction map of the riboswitch library according to one exemplary embodiment of the present disclosure is shown in FIG. 2.

To construct a library having the structure as described above, a cloning operation including the following procedures was performed as follows. Here, the respective procedures are schematically shown in FIG. 3.

(1) First, a tetA gene was subjected to PCR using a forward primer (SEQ ID NO: 7) having an SD sequence overhung with a KpnI restriction site, and a reverse primer (SEQ ID NO: 8)) having a linker sequence (Gly-Gly-Gly-Ser)×4 as an overhang. The PCR was performed under the following conditions: one cycle at 98° C. for 30 seconds, three cycles (at 98° C. for 10 seconds, at 55° C. for 15 seconds, and at 72° C. for 1 minute), and one cycle at 72° C. for 3 minutes, and the resulting PCR products were stored.

(2) Next, an sGFP gene was subjected to PCR using a forward primer (SEQ ID NO: 9) having a linker sequence (Gly-Gly-Gly-Ser)×4 as an overhang, and a reverse primer (SEQ ID NO: 10) having a SacI restriction site as an overhang.

(3) The respective PCR products were mixed, and subjected to overlap PCR to obtain a tetA-linker-sGFP gene. Specifically, the PCR products obtained in the procedures (1) and (2) were mixed, and subjected to PCR under the following PCR conditions: one cycle at 98° C. for 30 seconds, three cycles (at 98° C. for 10 seconds, at 60° C. for 30 seconds, and at 72° C. for 2 minutes), and one cycle at 72° C. for 5 minutes, and the resulting PCR products were stored. Thereafter, a forward primer (SEQ ID NO: 7) having an SD sequence overhung with a KpnI restriction site, and a reverse primer (SEQ ID NO: 10) having a SacI restriction site as an overhang was added, and the PCR was performed under the following conditions: one cycle at 98° C. for 30 seconds, 30 cycles (at 98° C. for 10 seconds, at 55° C. for 15 seconds, and at 72° C. for 2 minutes), and one cycle at 72° C. for 5 minutes, and the resulting PCR products were stored at 4° C.

Figure 4:
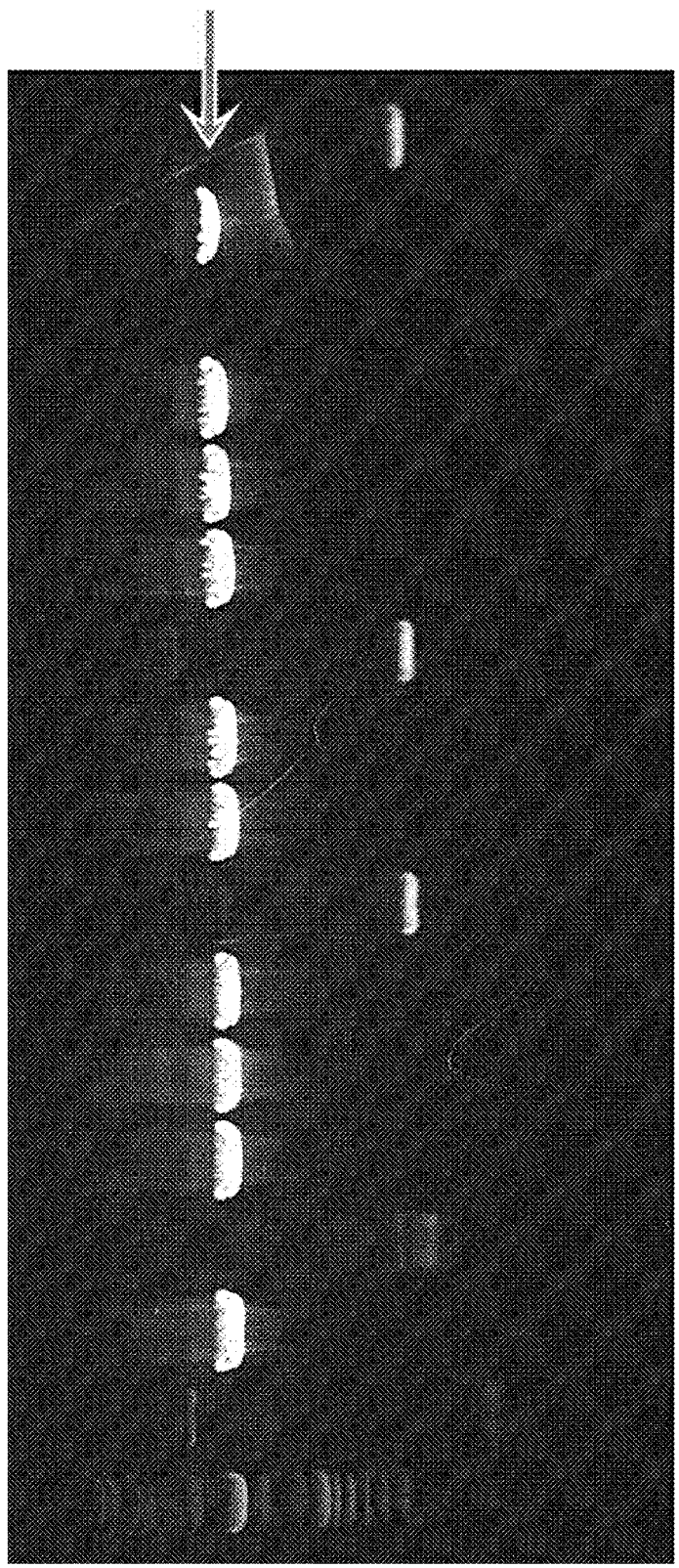
FIG. 4 shows the results of electrophoresis performed to determine the TA cloning results of pMD20-tetA-linker-sGFP.

(4) The tetA-linker-sGFP gene obtained in the procedure (3) was inserted into a T-vector. The gene inserted into the T-vector through the TA cloning was confirmed by PCR. The results are shown in FIG. 4. Specifically, the PCR products obtained in the procedures (1) and (2) were ligated through overlap PCR, and A-tails were added to both ends of the resulting constructs using a Taq polymerase so that the constructs were able to be ligated with the T-vector. As the final product, KpnI-SD-tetA-linker-sGFP-SacI was inserted into the T-vector. In this case, colony PCR was performed using a set of primers binding upstream and downstream from the inserted product. As shown in FIG. 4, a band having a length of approximately 1,959 bp was revealed when the product was accurately inserted.

Figure 5:
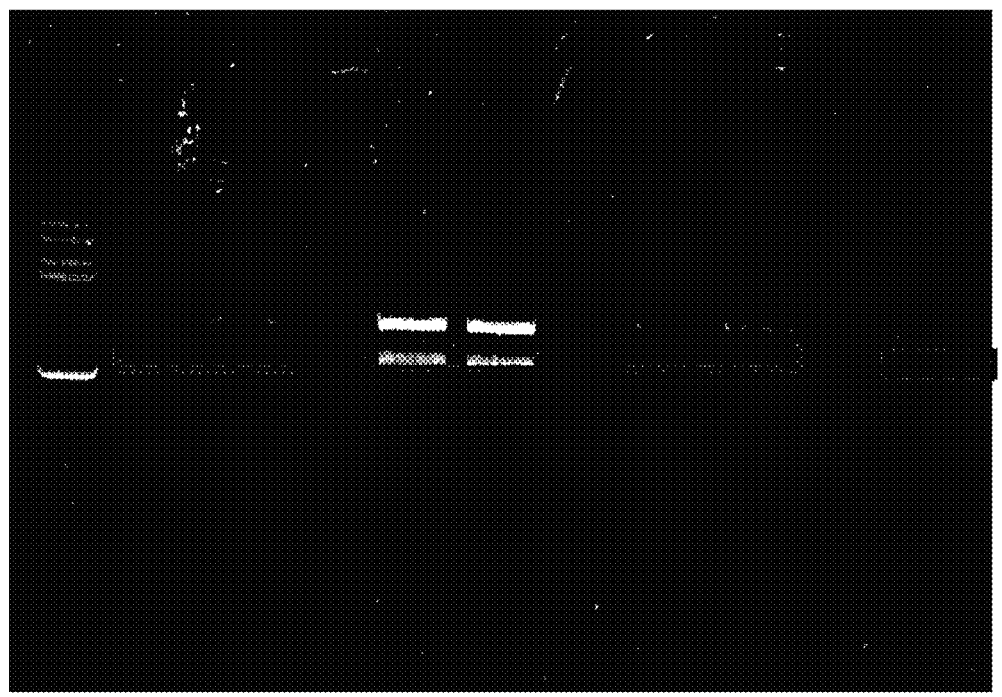
FIG. 5 shows the results obtained by performing electrophoresis on a tetA-linker-sGFP gene recovered after a vector into which a gene is cloned is digested by a restriction enzyme.

(5) A plasmid into which the construct was accurately inserted was selected through sequencing. When the plasmid obtained by inserting the construct into the T-vector was treated with restriction enzymes KpnI and SacI, restriction sites positioned at the 5'- and 3'-termini of the construct were digested to generate two fragments: a vector fragment and a construct fragment. The two fragments were recovered through gel electrophoresis. As shown in FIG. 5, it was revealed that the construct recovered by the present applicant was present in a band corresponding to a size of 1959 bp.

(6) Meanwhile, the pACYC Duet ΔlacI ΔT7 promoter plasmid was digested with restriction enzymes KpnI and SacI, and the gene was then recovered through gel electrophoresis.

Figure 6:
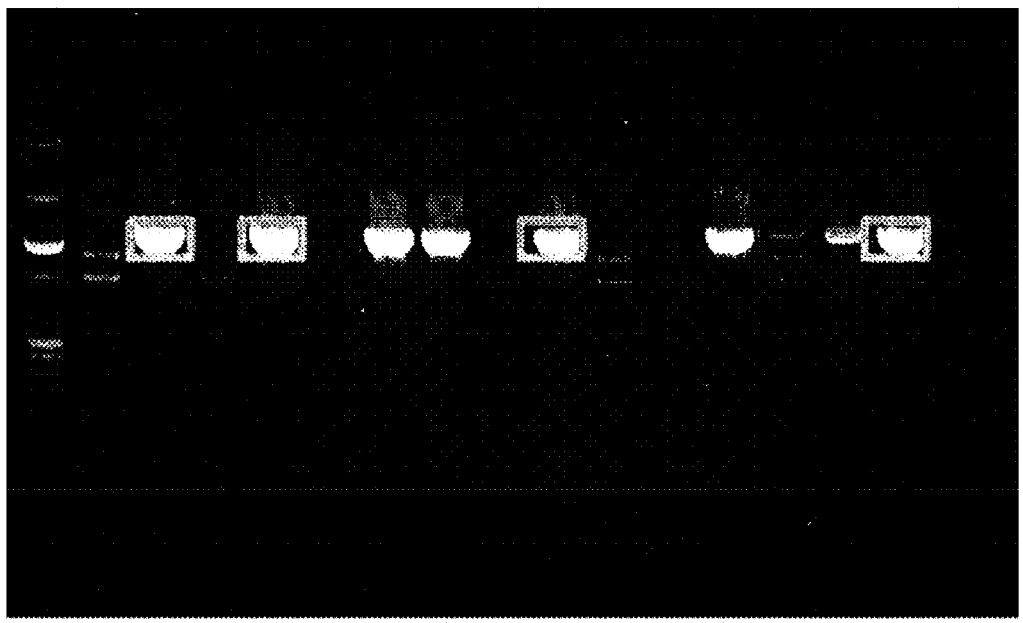
FIG. 6 shows the results obtained by performing electrophoresis after a pACYC Duet ΔlacI ΔT7 promoter plasmid is ligated with a tetA-linker-sGFP gene according to one exemplary embodiment of the present disclosure.

(7) Subsequently, the products obtained in the procedures (5) and (6) were ligated using a T4 ligase, and determined through electrophoresis. The results are shown in FIG. 6. Specifically, a plasmid in which a lad gene and a T7 promoter were deleted from a pACYC Duet vector was digested with restriction enzymes KpnI and SacI, and then ligated with the structure recovered in the procedure (5). Since the 5'- and 3'-termini of the construct were also digested with the restriction enzymes KpnI and SacI, the construct was able to be accurately ligated with pACYC. The results are shown in FIG. 6.

Figure 7:
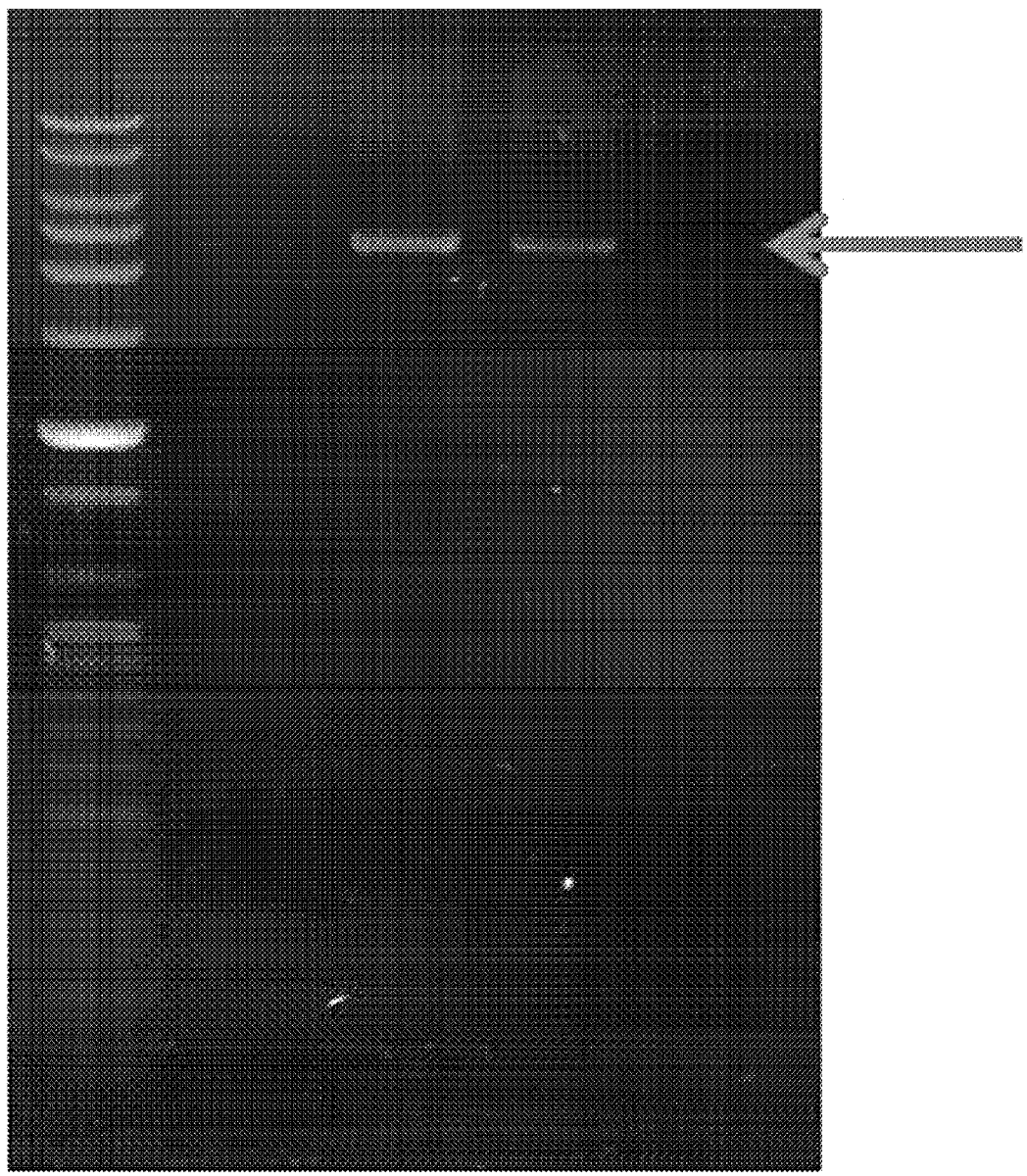
FIG. 7 shows the results obtained by performing PCR using a forward primer having a random sequence with a length of 10 bp overhung with a J23100 promoter, and a reverse primer complementarily binding to a pACYC Duet ΔlacI ΔT7 promoter according to one exemplary embodiment of the present disclosure.

(8) Then, PCR was performed using a forward primer (SEQ ID NO: 11) having a random sequence with a length of 10 bp overhung with a J23100 promoter, and a reverse primer (SEQ ID NO: 12) complementarily binding to a pACYC Duet ΔlacI ΔT7 promoter plasmid under the following PCR conditions: one cycle at 95° C. for 30 seconds, 30 cycles (at 95° C. for 30 seconds, at 56° C. for 30 seconds, and at 72° C. for 5 minutes), and one cycle at 72° C. for 7 minutes, and the resulting PCR products were stored at 4° C. The results are shown in FIG. 7. In a state in which tetA-linker-sGFP was inserted into pACYC, a forward primer was designed to insert an aptamer and a random sequence upstream from tetA, and a reverse primer was designed to bind upstream from tetA. When PCR was performed using the forward and reverse primers, a full-length pACYC-aptamer-random sequence-tetA-linker-sGFP gene was obtained. This linear DNA sequence was subjected to blunt end ligation to construct a plasmid. The plasmid was confirmed as shown in FIG. 7.

(9) Then, both ends of the plasmid construct obtained in the procedure (8) by the blunt-end ligation method were ligated to each other.

(10) The product obtained in the procedure (9) was transformed into MegaX DHα 10B cells. As a result, the riboswitch library according to one exemplary embodiment of the present disclosure was completely constructed.

EXAMPLE 2

Selection of L-Tryptophan-Specific Riboswitch

Riboswitches (RNA switches) responding to L-tryptophan were selected from the riboswitch library (an RNA switch library) constructed in Example 1 through the two selection procedures.

The nature of a tetA gene was used in the selection procedures. When the tetA gene was expressed, a tetA protein migrated into a cell membrane to discharge tetracycline from the cells. Thus, the cells were resistant to tetracycline. However, when the tetA gene was overexpressed, the cells died due to the presence of nickel ions. When the nature of the tetA gene was used as described above, it was possible to select the cells having a plasmid in which the tetA gene was overexpressed when L-tryptophan was present at a high concentration in the cells and was not expressed when L-tryptophan was present at a low concentration.

Figure 8:
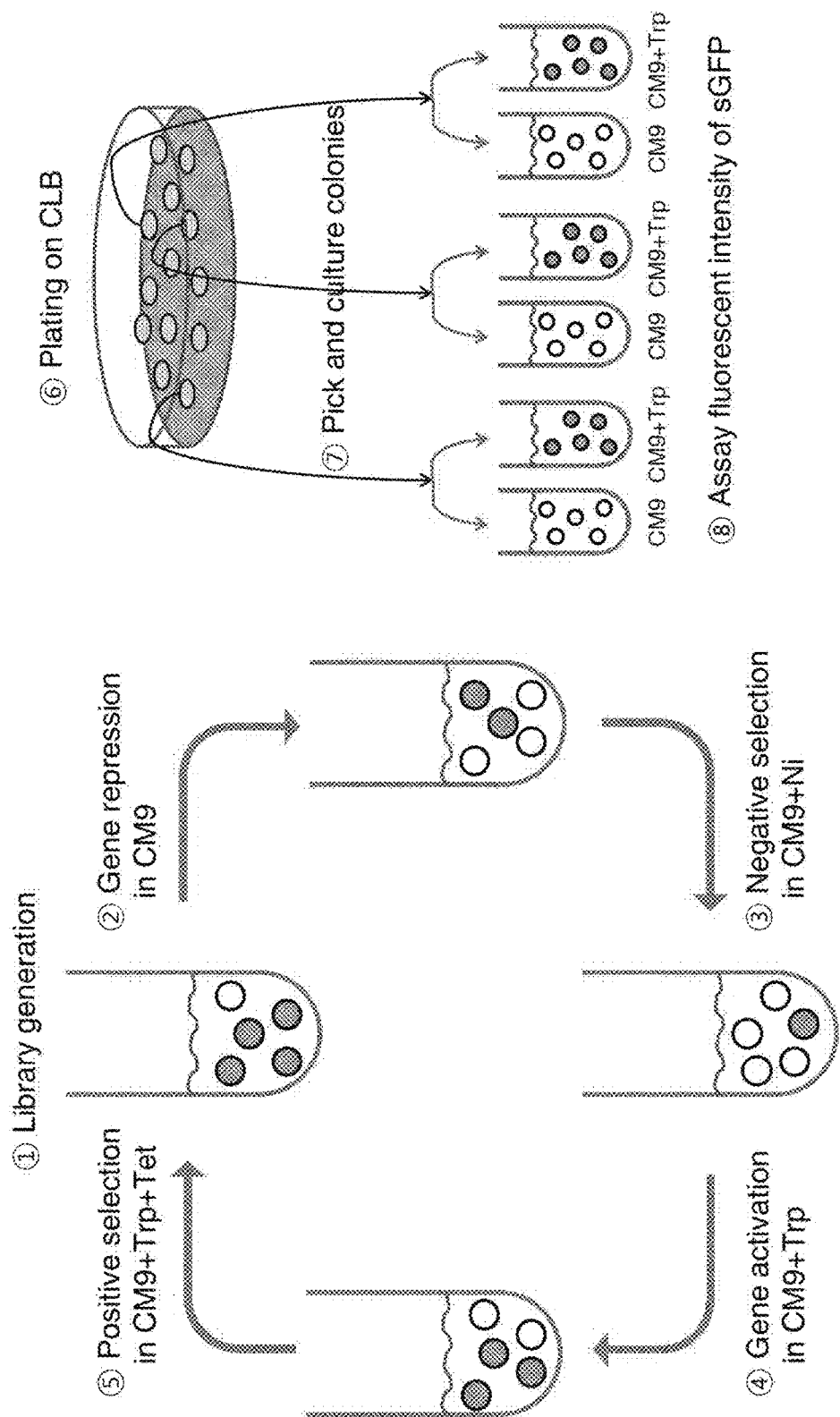
FIG. 8 is a schematic view showing a procedure of selecting a riboswitch specific to L-tryptophan from a riboswitch library according to one exemplary embodiment of the present disclosure.

A procedure of selecting an L-tryptophan-specific riboswitch is shown in FIG. 8. Such a selection procedure will be described in further detail, as follows. The cells surviving when tetracycline was added to a medium in a state in which L-tryptophan was present at a high concentration in the cells were cells in which the tetA gene was overexpressed. Such cells were harvested, and handled so that L-tryptophan was present in a low concentration in the cells. Then, the cells still surviving when nickel ions were added to a medium to grow the cells were able to be obtained (Adapted from Muranaka, N. et al., Nucl. Acids Res., 37, e39, 2009).

The cells surviving both selection procedures as described above contained a plasmid in which the tetA gene was expressed when L-tryptophan was present at a high concentration, but was not expressed when L-tryptophan was present at a low concentration. Such a plasmid was harvested and sequenced, it was confirmed which sequences among the random sequence having a size of 10 bp functioned as the riboswitches.

Meanwhile, the performance of each riboswitch was able to be measured using an sGFP gene ligated with each tetA gene. The ability of the riboswitch to regulate gene expression was examined by measuring the intensities of fluorescence emitted by sGFP when L-tryptophan was present at high and low concentrations in the cells.

The detailed experimental procedures were as follows.

(1) E. coli W3110 cells carrying a riboswitch library plasmid were cultured for 8 hours in an M9 medium supplemented with chloramphenicol, and the culture broth was transferred to a CM9 medium supplemented with 0.2 mM $NiCl_2$ and then cultured for 24 hours.

(2) The culture broth obtained in the procedure (1) was transferred to a CM9 medium supplemented with 1 mM L-tryptophan, and then cultured for 8 hours. The resulting culture broth was transferred to a CM9 medium supplemented with 1 mM L-tryptophan and tetracycline (40 or 100 μg/ml), and then cultured for 24 hours.

(3) The culture broth obtained in the procedure (2) was grown on a CLB plate in which an LB medium was supplemented with chloramphenicol. Some of the colonies formed on the CLB plate were selected, grown in media with/without L-tryptophan, and then measured for intensity of fluorescence.

Figure 9:
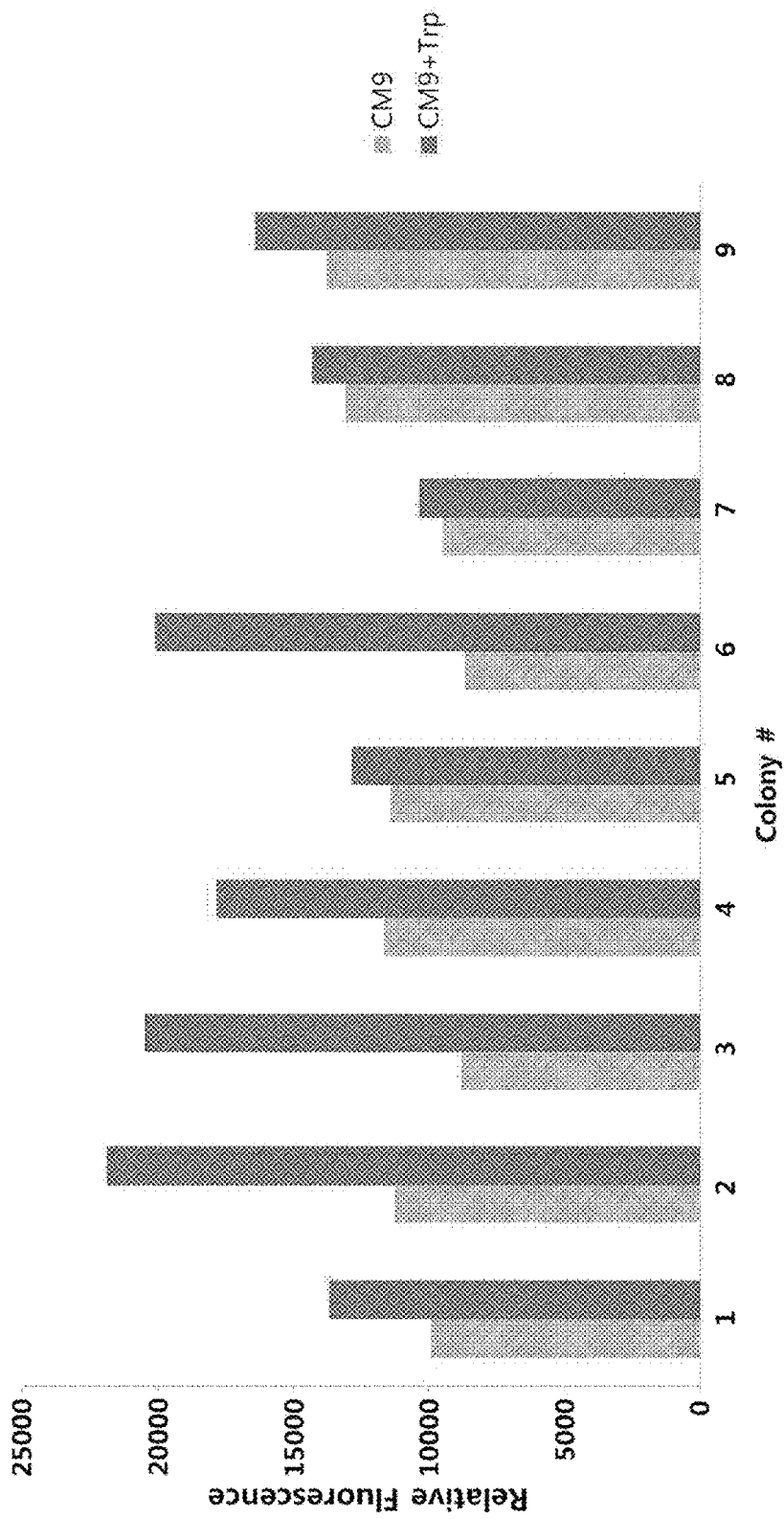
FIG. 9 shows the results obtained by measuring the performance of each riboswitch using an sGFP gene.

The experimental results are shown in FIG. 9. In FIG. 9, colonies 1 to 3 were cells selected in the presence of 40 μg/ml tetracycline, and colonies 4 to 9 were cells selected in the presence of 100 μg/ml tetracycline. As shown in FIG. 9, colonies 2, 3 and 6 showed good performance, and had an activation ratio of approximately 2.3. DNA sequences of colonies 2, 3 and 6 showing the good performance are set forth in SEQ ID NOS: 3, 4, and 5, respectively.

Meanwhile, colonies 2, 3 and 6 showing the good performance were sequenced. As a result, it was revealed that the tryptophan aptamers had different sequences. That is, the tryptophan aptamer had a sequence set forth in SEQ ID NO: 2 in the case of colony 3, and colonies 2 and 6 had sequences set forth in SEQ ID NOS: 13 and 15, respectively. From these results, it could be seen that mutations occurred during the selection.

The term "activation ratio" used herein refers to a ratio of a value normalized by subtracting a background fluorescence intensity from a fluorescence intensity of a cell culture when tryptophan is added and is not added to a medium, and dividing the resulting fluorescence intensity by an optical density (O.D.), and may be expressed, as follows. In the following Expression, however, the background fluorescence intensity is a value obtained by measuring a fluorescence intensity of phosphate buffered saline (PBS). In this case, the fluorescence intensity of PBS is used as the background fluorescence intensity because the medium was diluted with PBS when the fluorescence intensity of the cell culture was measured.

$$\text{activation ratio} = \frac{\frac{(\text{fluorescence of cell culture in the presence of tryptophan}) - (\text{background fluorescence})}{(O.D. \text{ of cell culture in the presence of tryptophan})}}{\frac{(\text{fluorescence of cell culture in the absence of tryptophan}) - (\text{background fluorescence})}{(O.D. \text{ of cell culture in the absence of tryptophan})}}$$

Figure 10:
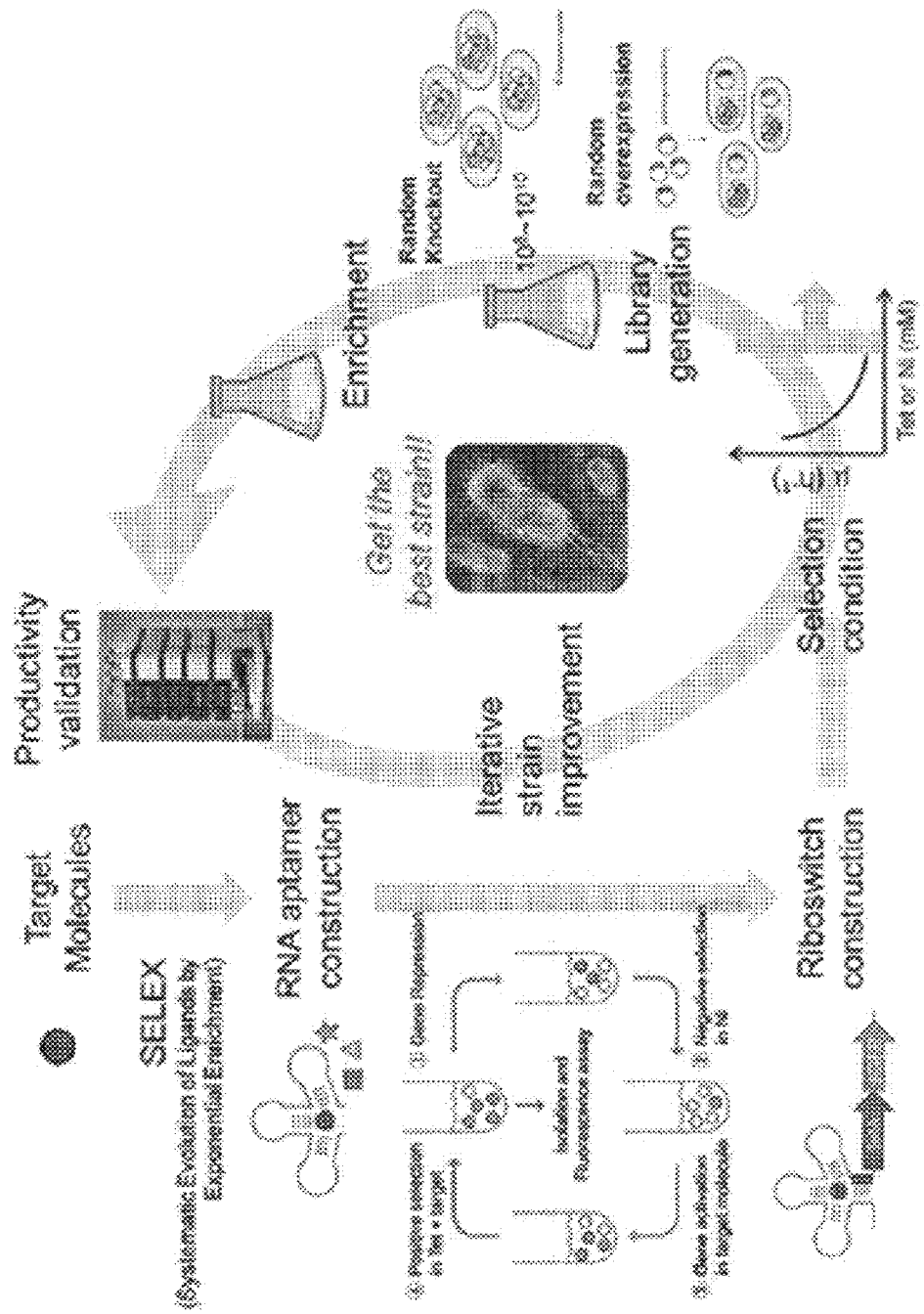
FIG. 10 is a schematic view showing a procedure of applying the technology provided in the present disclosure to various target materials.

The method of screening a high L-tryptophan-producing microorganism using the riboswitch prepared according to the exemplary embodiment of the present disclosure is schematically shown in FIG. 10.

The diagram shown in FIG. 10 shows a procedure of applying the technology provided in the present disclosure to various target materials. A superior strain was able to be obtained by performing a procedure of generating an RNA aptamer binding to a target material through a SELEX procedure, generating a riboswitch based on the generated aptamer, and enriching the target material in a strain library using the generated riboswitch. The strain obtained by such a method was able to be closely examined and immediately used to produce the target material, and the superior strain was able to be obtained by repeatedly performing the enrichment procedure several times.

The riboswitch according to one exemplary embodiment of the present disclosure and the method of screening a high L-tryptophan-producing microorganism using the same can be useful in selecting a strain producing a high concentration of L-tryptophan in a relatively quick and easy manner, and thus enhancing price competitiveness of tryptophan production using microorganisms.

INDUSTRIAL AVAILABILITY

The method of screening a high L-tryptophan-producing microorganism using the riboswitch according to one exemplary embodiment of the present disclosure can be useful in selecting a strain producing a high concentration of L-tryptophan in a relatively quick and easy manner, and thus producing tryptophan at a low price.

What is claimed is:

1. A riboswitch for screening a high L-tryptophan-producing microorganism, comprising:
   a tryptophan aptamer selected from the group consisting of SEQ ID NO: 2, SEQ ID NO: 13 and SEQ ID NO: 15,
   a DNA sequence selected from the group consisting of SEQ ID NO: 3, SEQ ID NO: 4 and SEQ ID NO: 5, and
   a selectable marker gene.

2. The riboswitch of claim 1, wherein the selectable marker gene is a tetA gene.

3. A method of screening a high L-tryptophan-producing microorganism, comprising preparing the riboswitch according to claim 1 and enriching a target material in a strain library with the riboswitch to obtain a superior strain.

4. The method of claim 3, wherein the selectable marker gene is a tetA gene.

* * * * *

SEQUENCE LISTING

```
<160> NUMBER OF SEQ ID NOS: 16

<210> SEQ ID NO 1
<211> LENGTH: 64
<212> TYPE: RNA
<213> ORGANISM: Artificial Sequence
<220> FEATURE:
<223> OTHER INFORMATION: L-tryptophan aptamer(Trp 70-727) : Colony #3

<400> SEQUENCE: 1
cuggacgacg gggacgccac uggacuaggu aagccaggac cguacgucgg gagccgucag      60
aaua                                                                  64

<210> SEQ ID NO 2
<211> LENGTH: 64
<212> TYPE: DNA
<213> ORGANISM: Artificial Sequence
<220> FEATURE:
<223> OTHER INFORMATION: L-tryptophan aptamer(Trp 70-727) : Colony #3

<400> SEQUENCE: 2
ctggacgacg gggacgccac tggactaggt aagccaggac cgtacgtcgg gagccgtcag      60
aata                                                                  64

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
gagggtaaga                                                            10

<210> SEQ ID NO 4
<211> LENGTH: 10
<212> TYPE: DNA
<213> ORGANISM: Artificial Sequence
<220> FEATURE:
<223> OTHER INFORMATION: Synthetic

<400> SEQUENCE: 4
tatatgggat                                                            10

<210> SEQ ID NO 5
<211> LENGTH: 10
<212> TYPE: DNA
<213> ORGANISM: Artificial Sequence
<220> FEATURE:
<223> OTHER INFORMATION: Synthetic
```

<400> SEQUENCE: 5 ctagaggggt					10

<210> SEQ ID NO 6
<211> LENGTH: 1954
<212> TYPE: DNA
<213> ORGANISM: Artificial Sequence
<220> FEATURE:
<223> OTHER INFORMATION: tetA-sGFP fusion gene

<400> SEQUENCE: 6

```
atgaaatcta acaatgcgct catcgtcatc ctcggcaccg tcaccctgga tgctgtaggc      60
v                                                                     61
ataggcttgg ttatgccggt actgccgggc ctcttgcggg atatcgtcca ttccgacagc     121
atcgccagtc actatggcgt gctgctagcg ctatatgcgt tgatgcaatt tctatgcgca     181
cccgttctcg gagcactgtc cgaccgcttt ggccgccgcc cagtcctgct cgcttcgcta     241
cttggagcca ctatcgacta cgcgatcatg gcgaccacac ccgtcctgtg gatcctctac     301
gccggacgca tcgtggccgg catcaccggc gccacaggtg cggttgctgg cgcctatatc     361
gccgacatca ccgatgggga agatcgggct cgccacttcg gctcatgagc gcttgttttc     421
ggcgtgggta tggtggcagg ccccgtggcc ggggactgtt gggcgccat ctccttgcat      481
gcaccattcc ttgcggcggc ggtgctcaac ggcctcaacc tactactggg ctgcttccta     541
atgcaggagt cgcataaggg agagcgtcga ccgatgccct tgagagcctt caacccagtc     601
agctccttcc ggtgggcgcg gggcatgact atcgtcgccg cacttatgac tgtcttcttt     661
atcatgcaac tcgtaggaca ggtgccggca gcgctctggg tcattttcgg cgaggaccgc     721
tttcgctgga gcgcgacgat gatcggcctg tcgcttgcgg tattcggaat cttgcacgcc     781
ctcgctcaag ccttcgtcac tggtcccgcc accaaacgtt tcggcgagaa gcaggccatt     841
atcgccggca tggcggccga cgcgctgggc tacgtcttgc tggcgttcgc gacgcgaggc     901
tggatggcct tccccattat gattcttctc gcttccggcg gcatcgggat gccgcgttg     961
caggccatgc tgtccaggca ggtagatgac gaccatcagg gacagcttca aggatcgctc    1021
gcggctctta ccagcctaac ttcgatcact ggaccgctga tcgtcacggc gatttatgcc    1081
gcctcggcga gcacatggaa cgggttggca tggattgtag gcgccgccct ataccttgtc    1141
tgcctccccg cgttgcgtcg cggtgcatgg agccgggcca cctcgaccgg cggtgggtcg    1201
ggcggtgggt ccggcggtgg gagtggcggt gggagcgcta gcaagggcga ggagctgttc    1261
accggggtgg tgcccatcct ggtcgagctg gacggcgacg taaacggcca aagttcagc     1321
gtgcgcggcg agggcgaggg cgatgccacc aacggcaagc tgaccctgaa gttcatctgc    1381
accaccggca agctgcccgt gccctggccc accctcgtga ccaccctgac ctacggcgtg    1441
cagtgcttca gccgctaccc cgaccacatg aagcagcacg acttcttcaa gtccgccatg    1501
cccgaaggct acgtccagga gcgcaccatc agcttcaagg acgacggcac ctacaagacc    1561
cgcgccgagg tgaagttcga gggcgacacc ctggtgaacc gcatcgagct gaagggcatc    1621
gacttcaagg aggacggcaa catcctgggg cacaagctgg agtacaactt caacagccac    1681
aacgtctata tcaccgccga caagcagaag aacggcatca aggccaactt caagatccgc    1741
cacaacgtgg aggacggcag cgtgcagctc gccgaccact accagcagaa cacccccatc    1801
ggcgacggcc ccgtgctgct gcccgacaac cactacctga gcacccagtc cgtgctgagc    1861
aaagacccca acgagaagcg cgatcacatg gtcctgctgg agttcgtgac cgccgccggg    1921
```
atcactctcg gcatggacga gctgtacaag tga                                  1954

<210> SEQ ID NO 7
<211> LENGTH: 45
<212> TYPE: DNA
<213> ORGANISM: Artificial Sequence
<220> FEATURE:
<223> OTHER INFORMATION: forward primer : KpnI site-SD sequence-Start
      of tetA

<400> SEQUENCE: 7
ggtaccaagg agcatctatg aaatctaaca atgcgctcat cgtca                       45

<210> SEQ ID NO 8
<211> LENGTH: 66
<212> TYPE: DNA
<213> ORGANISM: Artificial Sequence
<220> FEATURE:
<223> OTHER INFORMATION: reverse primer : (GGGS)4 linker-Start of sGFP
      without start codon

<400> SEQUENCE: 8
gctcccaccg ccactcccac cgccggaccc accgcccgac ccaccgccgg tcgaggtggc       60
ccggct                                                                 66

<210> SEQ ID NO 9
<211> LENGTH: 68
<212> TYPE: DNA
<213> ORGANISM: Artificial Sequence
<220> FEATURE:
<223> OTHER INFORMATION: forward primer : (GGGS)4 linker-Start of sGFP
      without start codon

<400> SEQUENCE: 9
ggcggtgggt cgggcggtgg gtccggcggt gggagtggcg gtgggagcgc tagcaagggc       60
gaggagct                                                               68

<210> SEQ ID NO 10
<211> LENGTH: 30
<212> TYPE: DNA
<213> ORGANISM: Artificial Sequence
<220> FEATURE:
<223> OTHER INFORMATION: reverse primer : SacI site-End of sGFP

<400> SEQUENCE: 10
gagctctcac ttgtacagct cgtccatgcc                                       30

<210> SEQ ID NO 11
<211> LENGTH: 140
<212> TYPE: DNA
<213> ORGANISM: Artificial Sequence
<220> FEATURE:
<223> OTHER INFORMATION: forward primer : J23100 promoter-Trp70-727
      aptamer-N10 random sequence-SD sequence-start of tetA
<220> FEATURE:
<221> NAME/KEY: Variation
<222> LOCATION: (100)...(109)
<223> OTHER INFORMATION: a, t, c or g

<400> SEQUENCE: 11
ttgacggcta gctcagtcct aggtacagtg ctagcctgga cgacggggac gccactggac       60
taggtaagcc aggaccgtac gtcgggagcc gtcagaatan nnnnnnnna aggagcatct      120 atgaaatcta acaatgcgct                                                 140

```
<210> SEQ ID NO 12
<211> LENGTH: 30
<212> TYPE: DNA
<213> ORGANISM: Artificial Sequence
<220> FEATURE:
<223> OTHER INFORMATION: reverse primer : SacI site-End of pACYC

<400> SEQUENCE: 12
ggtaccgcgc aacgcaatta atgtaagtta                                            30

<210> SEQ ID NO 13
<211> LENGTH: 64
<212> TYPE: DNA
<213> ORGANISM: Artificial Sequence
<220> FEATURE:
<223> OTHER INFORMATION: L-tryptophan aptamer : Colony #2

<400> SEQUENCE: 13
ctggacgacg gggacgccac tggactaagg taaccaggac cgtacgtcgg gagccgtcag           60
aata                                                                        64

<210> SEQ ID NO 14
<211> LENGTH: 64
<212> TYPE: RNA
<213> ORGANISM: Artificial Sequence
<220> FEATURE:
<223> OTHER INFORMATION: L-tryptophan aptamer : Colony #2

<400> SEQUENCE: 14
cuggacgacg gggacgccac uggacuaagg uaaccaggac cguacgucgg gagccgucag           60
aaua                                                                        64

<210> SEQ ID NO 15
<211> LENGTH: 63
<212> TYPE: DNA
<213> ORGANISM: Artificial Sequence
<220> FEATURE:
<223> OTHER INFORMATION: L-tryptophan aptamer : Colony #6

<400> SEQUENCE: 15
ctggacgacg gggacgccac tggactaggt aaggccagga ccgtacgtcg ggagccgtga           60
ata                                                                         63

<210> SEQ ID NO 16
<211> LENGTH: 63
<212> TYPE: RNA
<213> ORGANISM: Artificial Sequence
<220> FEATURE:
<223> OTHER INFORMATION: L-tryptophan aptamer : Colony #6

<400> SEQUENCE: 16
cuggacgacg gggacgccac uggacuaggu aaggccagga ccguacgucg ggagccguga           60
aua                                                                         63
```